US011130930B2

(12) United States Patent
Farvid et al.

(10) Patent No.: US 11,130,930 B2
(45) Date of Patent: Sep. 28, 2021

(54) COMPOSITIONS FOR TREATMENT AND METHODS FOR MAKING AND USING THE SAME

(71) Applicant: ASP Global Manufacturing GmbH, Schaffhausen (CH)

(72) Inventors: Shokouh Farvid, Irvine, CA (US); Navid Omidbakhsh, Irvine, CA (US); Keyvan Nowruzi, Irvine, CA (US)

(73) Assignee: ASP GLOBAL MANUFACTURING GMBH, Shaffhausen (CH)

( * ) Notice: Subject to any disclaimer, the term of this patent is extended or adjusted under 35 U.S.C. 154(b) by 0 days.

(21) Appl. No.: 16/452,899

(22) Filed: Jun. 26, 2019

(65) Prior Publication Data

US 2020/0002647 A1 Jan. 2, 2020

Related U.S. Application Data

(60) Provisional application No. 62/691,224, filed on Jun. 28, 2018.

(51) Int. Cl.
| | |
|---|---|
| *C11D 3/48* | (2006.01) |
| *A61B 90/70* | (2016.01) |
| *B08B 3/08* | (2006.01) |
| *C11D 3/12* | (2006.01) |
| *C11D 3/30* | (2006.01) |
| *C11D 3/34* | (2006.01) |
| *C11D 3/386* | (2006.01) |
| *C11D 3/43* | (2006.01) |
| *A01N 63/50* | (2020.01) |

(52) U.S. Cl.
CPC ............... *C11D 3/48* (2013.01); *A01N 63/50* (2020.01); *A61B 90/70* (2016.02); *B08B 3/08* (2013.01); *C11D 3/12* (2013.01); *C11D 3/30* (2013.01); *C11D 3/3418* (2013.01); *C11D 3/38618* (2013.01); *C11D 3/43* (2013.01); *A61B 2090/701* (2016.02)

(58) Field of Classification Search
CPC ........... C11D 3/30; C11D 3/12; C11D 3/3418; C11D 3/38618; C11D 3/48; C11D 3/386; C11D 11/0094; A61B 90/70; B08B 3/08
See application file for complete search history.

(56) References Cited

U.S. PATENT DOCUMENTS

2014/0256025 A1  9/2014  Esquenet et al.

FOREIGN PATENT DOCUMENTS

| WO | WO 2017/124150 A1 | 7/2017 |
| WO | WO 2017/192417 A1 | 11/2017 |

OTHER PUBLICATIONS

International Search Report and Written Opinion of PCT/IB2019/000845, dated Dec. 4, 2019.
Anios Laboratories, Aniosyme DD1 Material Safety Data Sheet, Version: 2, Aug. 31, 2007, 8 pages.
Anios Laboratories, Aniosyme DD1 Cleaning and Pre-Disinfection of Instrumetation, date not available, 2 pages.
Advanced Sterilization Products, Enzol Enzymatic Detergent Material Safety Data Sheet, Oct. 3, 2007, 6 pages.
Metrex Research, Empower Material Safety Data Sheet, Jan. 2011, 7 pages.
The Ruhof Corporation, Endozime AW Plus with A.P.A. Material Safety Data Sheet, Mar. 15, 2016, 2 pages.
Steris Corporation, Prolystica 2X Concentrate Neutral Detergent Material Safety Data Sheet, Mar. 9, 2017, 6 pages.
Martin J. Schick, "Handbook of detergents part D: formulation", Surfactant Science Series, Taylor & Francis group, LLC, 2006, p. 79.
Marcel Decker, "Handbook of Detergent, part A: properties", Surfactant Science Series, 1999, p. 675, vol. 82, ISBN: 0-8247-1417-2.
Borates in Detergents and Cleaners available at https://www.borax.com/applications/cleaners-detergents (accessed Oct. 16, 2020).

*Primary Examiner* — Natasha N Campbell
(74) *Attorney, Agent, or Firm* — K&L Gates LLP

(57) ABSTRACT

A detergent composition, a method of making the detergent composition, and a method of use thereof are provided. The detergent composition comprises at least 0.001% by weight of an antimicrobial agent, based on the total weight of the composition; an enzyme; and at least 0.01% by weight of a hydrotrope, based on the total weight of the composition.

24 Claims, 5 Drawing Sheets
(4 of 5 Drawing Sheet(s) Filed in Color)

1% AX + 5% CHG  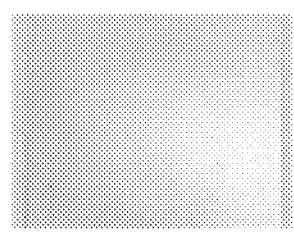   1% AX, no CHG 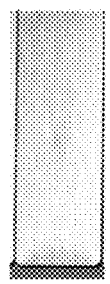 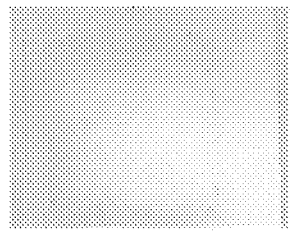
FIG. 2A     FIG. 2B         FIG. 2C     FIG. 2D
0.4% C1 + 5% CHG 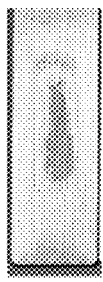 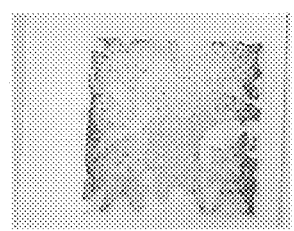   0.4% C1, no CHG 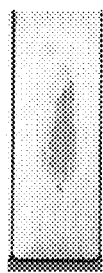 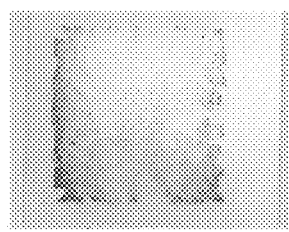
FIG. 3A     FIG. 3B         FIG. 3C     FIG. 3D

| 0.8% C2 + 5% CHG | 0.8% C2, no CHG |
| CHG is insoluble | CHG is insoluble | 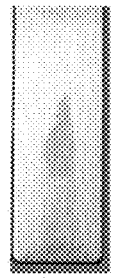 | 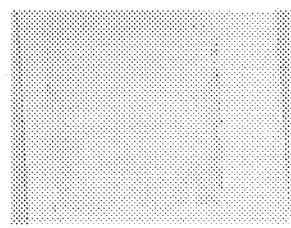 |
| FIG. 4A | FIG. 4B | FIG. 4C | FIG. 4D |
| 0.4% C3 + 5% CHG | 0.4% C3, no CHG |
| CHG is insoluble | CHG is insoluble | 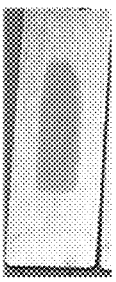 | 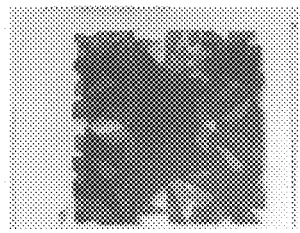 |
| FIG. 5A | FIG. 5B | FIG. 5C | FIG. 5D |

0.5% C4 + 5% CHG    0.5% C4, no CHG
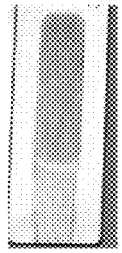 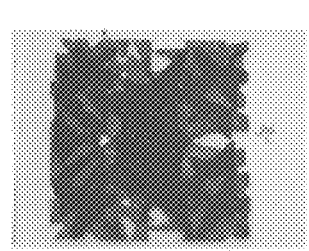 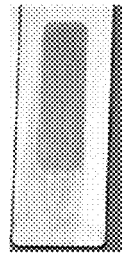 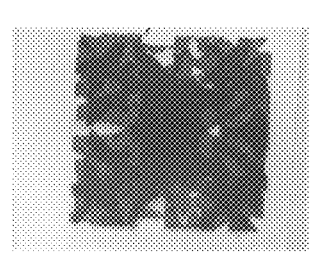
FIG. 6A    FIG. 6B    FIG. 6C    FIG. 6D
0.4% C5 + 5% CHG    0.4% C5, no CHG
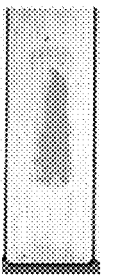 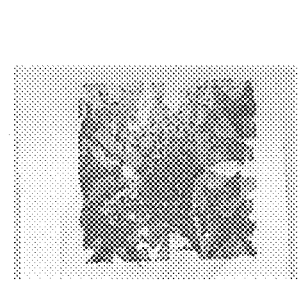 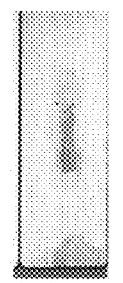 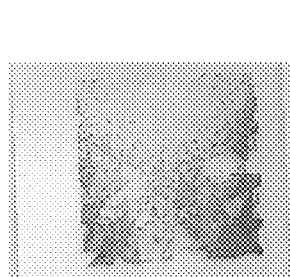
FIG. 7A    FIG. 7B    FIG. 7C    FIG. 7D

| 0.8% C6 + 5% CHG | | 0.8% C6, no CHG | |
|---|---|---|---|
| CHG is insoluble | CHG is insoluble | 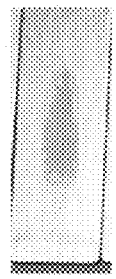 | 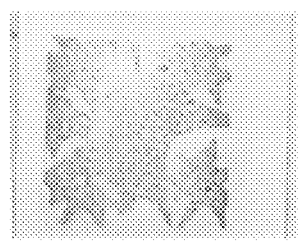 |
| FIG. 8A | FIG. 8B | FIG. 8C | FIG. 8D |

COMPOSITIONS FOR TREATMENT AND METHODS FOR MAKING AND USING THE SAME

CROSS REFERENCE TO RELATED APPLICATIONS

This application claims the benefit of U.S. Provisional Application No. 62/691,224 filed Jun. 28, 2018, which is incorporated herein by reference.

FIELD

The present disclosure relates to compositions for treatment and methods of making and using those compositions.

BACKGROUND

Various medical devices are employed for procedures in the medical field. One such device is an endoscope that examines the interior of a hollow organ or cavity of the body. Ensuring reusable medical devices are treated property can inhibit or prevent cross-contamination and the spread of disease. In this regard, treatment solutions such as, for example, cleaning solutions and/or antimicrobial solutions are used on medical devices and facility surfaces.

SUMMARY

In one aspect, the present disclosure provides a detergent composition. The detergent composition comprises at least 0.001% by weight of an antimicrobial agent, based on the total weight of the composition, an enzyme, and at least 0.01% by weight of a hydrotrope, based on the total weight of the composition.

In another aspect, the present disclosure provides a method of making a detergent composition. The method comprises combining, based on the total weight of the composition, at least 0.001% by weight of an antimicrobial agent, at least 0.01% by weight of a hydrotrope, and an enzyme.

In yet another aspect, the present disclosure provides a method for cleaning an object. The method comprises applying a detergent composition to the object, thereby cleaning the object. The detergent composition comprises, based on the total weight of the composition, at least 0.001% by weight of an antimicrobial agent, at least 0.01% by weight of a hydrotrope, and an enzyme.

It is understood that the inventions described in this specification are not limited to the examples provided in this Summary. Various other aspects are described and exemplified herein.

BRIEF DESCRIPTION OF THE DRAWINGS

The present disclosure contains at least one drawing executed in color. Copies of the present disclosure with color drawing(s) will be provided by the Office upon request and payment of the necessary fee.

The features and advantages of the examples, and the manner of attaining them, will become more apparent and the examples will be better understood by reference to the following description of examples taken in conjunction with the accompanying drawings, wherein:

FIG. 2A-D shows photographs of plastic or stainless steel coupons treated with a diluted detergent composition according to the present disclosure.

FIG. 2A shows a photograph of a stainless steel coupon treated with a diluted detergent composition according to the present disclosure that was supplemented with chlorhexidine gluconate (CHG).

FIG. 2B shows a photograph of a plastic coupon treated with a diluted detergent composition according to the present disclosure that was supplemented with CHG.

FIG. 2C shows a photograph of a stainless steel coupon treated with a diluted detergent composition according to the present disclosure that was not supplemented with CHG.

FIG. 2D shows a photograph of a plastic coupon treated with a diluted detergent composition according to the present disclosure that was not supplemented with CHG.

FIG. 3A-D shows photographs of plastic or stainless steel coupons treated with a diluted detergent composition, C1.

FIG. 3A shows a photograph of a stainless steel coupon treated with a diluted detergent composition, C1, which was supplemented with CHG.

FIG. 3B shows a photograph of a plastic coupon treated with a diluted detergent composition, C1, which was supplemented with CHG.

FIG. 3C shows a photograph of a stainless steel coupon treated with a diluted detergent composition, C1, which was not supplemented with CHG.

FIG. 3D shows a photograph of a plastic coupon treated with a diluted detergent composition, C1, which was not supplemented with CHG.

FIG. 4A-D shows photographs, when available, of plastic or stainless steel coupons treated with a diluted detergent composition, C2.

FIG. 4A indicates that CHG was insoluble in a diluted detergent composition, C2.

FIG. 4B indicates that CHG was insoluble in a diluted detergent composition, C2.

FIG. 4C shows a photograph of a stainless steel coupon treated with a diluted detergent composition, C2, which was not supplemented with CHG.

FIG. 4D shows a photograph of a plastic coupon treated with a diluted detergent composition, C2, which was not supplemented with CHG.

FIG. 5A-D shows photographs, when available, of plastic or stainless steel coupons treated with a diluted detergent composition, C3.

FIG. 5A indicates that CHG was insoluble in a diluted detergent composition, C3.

FIG. 5B indicates that CHG was insoluble in a diluted detergent composition, C3.

FIG. 5C shows a photograph of a stainless steel coupon treated with a diluted detergent composition, C3, which was not supplemented with CHG.

FIG. 5D shows a photograph of a plastic coupon treated with a diluted detergent composition, C3, which was not supplemented with CHG.

FIG. 6A-D shows photographs of plastic or stainless steel coupons treated with a diluted detergent composition, C4.

FIG. 6A shows a photograph of a stainless steel coupon treated with a diluted detergent composition, C4, which was supplemented with CHG.

FIG. 6B shows a photograph of a plastic coupon treated with a diluted detergent composition, C4, which was supplemented with CHG.

FIG. 6C shows a photograph of a stainless steel coupon treated with a diluted detergent composition, C4, which was not supplemented with CHG.

FIG. 6D shows a photograph of a plastic coupon treated with a diluted detergent composition, C4, which was not supplemented with CHG.

FIG. 7A-D shows photographs of plastic or stainless steel coupons treated with a diluted detergent composition, C5.

FIG. 7A shows a photograph of a stainless steel coupon treated with a diluted detergent composition, C5, which was supplemented with CHG.

FIG. 7B shows a photograph of a plastic coupon treated with a diluted detergent composition, C5, which was supplemented with CHG.

FIG. 7C shows a photograph of a stainless steel coupon treated with a diluted detergent composition, C5, which was not supplemented with CHG.

FIG. 7D shows a photograph of a plastic coupon treated with a diluted detergent composition, C5, which was not supplemented with CHG.

FIG. 8A-D shows photographs, when available, of plastic or stainless steel coupons treated with a diluted detergent composition, C6.

FIG. 8A indicates that CHG was insoluble in a diluted detergent composition, C6.

FIG. 8B indicates that CHG was insoluble in a diluted detergent composition, C6.

FIG. 8C shows a photograph of a stainless steel coupon treated with a diluted detergent composition, C6, which was not supplemented with CHG.

FIG. 8D shows a photograph of a plastic coupon treated with a diluted detergent composition, C6, which was not supplemented with CHG.

Corresponding reference characters indicate corresponding parts throughout the several views. The exemplifications set out herein illustrate certain examples, in one form, and such exemplifications are not to be construed as limiting the scope of the examples in any manner.

DETAILED DESCRIPTION

Figure 1:
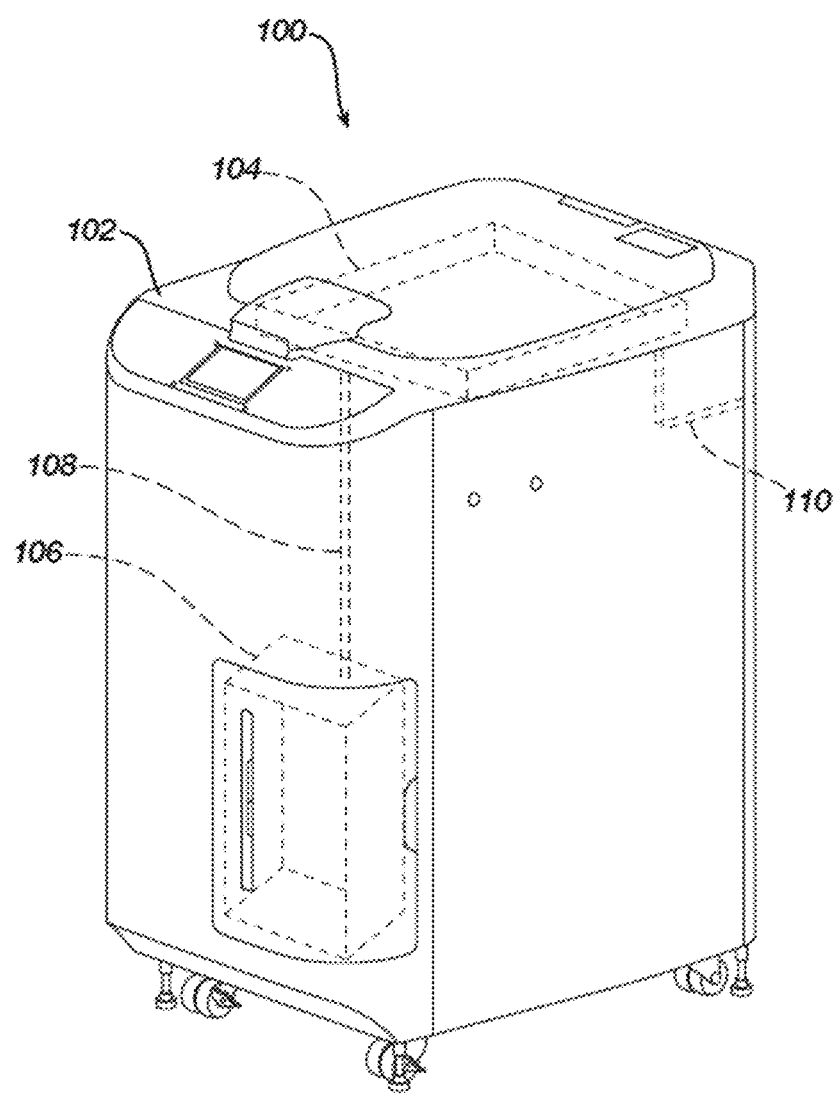
FIG. 1 is a depiction of a system for treatment of an object utilizing a detergent composition according to the present disclosure.

Certain exemplary aspects of the present disclosure will now be described to provide an overall understanding of the principles of the composition, function, manufacture, and use of the compositions and methods disclosed herein. One or more examples of these aspects are illustrated in the accompanying drawing. Those of ordinary skill in the art will understand that the compositions and methods specifically described herein and illustrated in the accompanying drawings are non-limiting exemplary aspects and that the scope of the various examples of the present invention is defined solely by the claims. The features illustrated or described in connection with one exemplary aspect may be combined with the features of other aspects. Such modifications and variations are intended to be included within the scope of the present invention.

Reference throughout the specification to "various examples," "some examples," "one example," or "an example", or the like, means that a particular feature, structure, or characteristic described in connection with the example is included in at least one example. Thus, appearances of the phrases "in various examples," "in some examples," "in one example", or "in an example", or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features structures, or characteristics of one or more other examples without limitation. Such modifications and variations are intended to be included within the scope of the present examples.

In this specification, unless otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification such that amending to expressly recite any such sub-ranges would comply with the requirements of 35 U.S.C. § 112 and 35 U.S.C. § 132(a).

The present disclosure relates to compositions for treatment and methods of making and using those compositions. Objects of the present disclosure can undergo a treatment process as set forth herein to prevent cross-contamination and the spread of disease. As used herein, a "treatment process" may be a cleaning process, a disinfecting process, the like, and combinations thereof. A treatment process may be either manual, automated, or some combination thereof, and may utilize a treatment agent. As used herein, a "treatment agent" can comprise at least one of a cleaning agent and an antimicrobial agent. As used herein a "cleaning process" means a treatment process employing a cleaning agent that removes and/or eliminates debris such as, for example, a body fluid (e.g., blood, urine, saliva) a dirt, a dust, a particle, an oil, a protein, a carbohydrate, and the like. As used herein, a "cleaning agent" means a type of treatment agent that removes and/or eliminates debris during a cleaning process such as, for example, a surfactant and/or a detergent.

A disinfecting process can remove and/or eliminate a bioburden from an object. A bioburden may be, for example, a bacterium (e.g., *mycobacterium*, bacterial spores), an archaeon, a eukaryote, a virus, a fungus, and/or other forms of biological agents. Bacterial spores (e.g., endospores) are a form of bacteria which are dormant and highly resistant to physical and chemical degradation. As used herein, a "disinfecting process" means a treatment process that substantially removes a bioburden. As used herein, "substantially remove" means that at least 99% of the bioburden has been removed from the object such as, for example, at least 99.9% of the bioburden, at least 99.99% of the bioburden, at least 99.999% of the bioburden, or at least 99.9999% of the bioburden has been removed from the object. The disinfection process may include, for example, the addition of heat, an antimicrobial agent, irradiation, pressure, and combinations thereof. The antimicrobial agent may comprise a chemical capable of disinfection.

As used herein, a "component" of the detergent composition of the present disclosure is meant to mean any chemical substance that can be added and/or can be a part of the detergent composition. For example, a component of the detergent composition can be water, an alcohol, an antimicrobial agent, a hydrotrope, a surfactant, a buffer, a solvent, an enzyme, a chelating agent, a salt, the like, and combinations thereof.

Detergent compositions comprising an enzyme can aid in cleaning an object. The enzyme can remove and/or eliminate debris. However, the enzyme, by itself, may not provide a sufficient reduction of bioburden to disinfect an object. Thus, an additional disinfecting process employing an antimicrobial agent can be performed simultaneously with or subsequent to the first cleaning step to prepare the object for subsequent use.

However, it was previously believed by those of ordinary skill in the art that an antimicrobial agent reduces the enzymatic activity of the enzyme of the detergent composition, possibly via denaturation of the enzyme's three-dimensional structure, thereby adversely affecting and diminishing the ability of the enzyme to remove and/or eliminate debris and/or bioburden. Additionally, the antimicrobial agent was thought to similarly denature elements of debris and/or bioburden making them less likely to be removed during a treatment process. Thus, previously, it was believed that an antimicrobial agent was incompatible with a detergent comprising an enzyme.

Surprisingly, it has been found that the addition of an antimicrobial agent to a detergent composition in combinations and/or amounts provided herein can enable a detergent composition already used for cleaning to also be used for disinfection processes. Thus, it has been found that the cleaning and disinfecting processes can be combined, and the efficiency of treating objects can be increased. The cleaning and disinfecting can be combined.

Accordingly, provided herein are detergent compositions comprising an antimicrobial agent and an enzyme, methods of making the detergent compositions, and methods of using the detergent compositions. The detergent compositions of the present disclosure can comprise a cleaning agent and an antimicrobial agent. The detergent compositions of the present disclosure can comprise an enzyme that can effectively remove and/or eliminate debris and/or bioburden from an object in the presence of an antimicrobial agent that can disinfect the object. The detergent compositions set forth herein can clean and disinfect the object.

In one example, the present disclosure provides a detergent composition comprising an antimicrobial agent, an enzyme, and a hydrotrope.

The antimicrobial agent can comprise at least one of a biguanide compound and a quaternary ammonium compound. Quaternary ammonium compounds comprise a nitrogen atom covalently bonded to four R-groups. For example, quaternary ammonium compounds can comprise Formula 1 below.

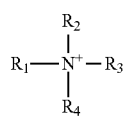

Formula 1 where $R_{1-4}$ are each an alkyl or aryl group, and $R_{1-4}$ may each be the same or different.

As used herein a "biguanide compound" means at least one of a bisbiguanide compound, a biguanide compound, and a polybiguanide compound. Polybiguanide compounds can comprise Formula 2 below.

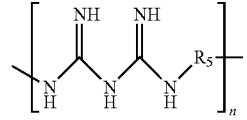

Formula 2 where $R_5$ is an alkyl or an aryl, $R_5$ may be halogen substituted; and n is in a range of 1 to 50.

For example, when n is 2, the polybiguanide compounds can comprise Formula 3 below.

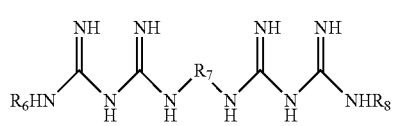

Formula 3 where $R_6$ and $R_8$ are each an alkyl or an aryl, $R_6$ and $R_8$ may be halogen substituted, and $R_6$ and $R_8$ may be the same or different; and $R_7$ is an alkyl comprising 3 to 10 carbon atoms.

The antimicrobial agent in the detergent compositions of the present disclosure can remove and/or eliminate bioburden. The antimicrobial agent can disinfect an object (e.g., via disruption of biological membranes or denaturation of proteins). The antimicrobial agent can be present in the detergent compositions of the present disclosure in any effective amount. For example, the detergent composition can comprise at least 0.001% antimicrobial agent by weight based on the total weight of the detergent composition such as, for example, at least 0.01% antimicrobial agent by weight, at least 0.1% antimicrobial agent by weight, at least 0.5% antimicrobial agent by weight, at least 1% antimicrobial agent by weight, at least 2% antimicrobial agent by weight, at least 3% antimicrobial agent by weight, at least 4% antimicrobial agent by weight, at least 5% antimicrobial agent by weight, at least 10% antimicrobial agent by weight, or at least 15% antimicrobial agent by weight. The detergent composition can comprise 20% or less antimicrobial agent by weight based on the total weight of the detergent composition such as, for example, 15% or less antimicrobial agent by weight, 10% or less antimicrobial agent by weight, 5% or less antimicrobial agent by weight, 4% or less antimicrobial agent by weight, 3% or less antimicrobial agent by weight, 2% or less antimicrobial agent by weight, 1% or less antimicrobial agent by weight, 0.5% or less antimicrobial agent by weight, 0.1% or less antimicrobial agent by weight, or 0.01% or less antimicrobial agent by weight. The detergent composition can comprise 0.001% to 20% antimicrobial agent by weight based on the total weight of the detergent composition such as, for example, 0.001% to 5% antimicrobial agent by weight, 0.01% to 5% antimicrobial agent by weight, 0.1% to 5% antimicrobial agent by weight, 1% to 5% antimicrobial agent by weight, 1% to 10% antimicrobial agent by weight, 5% to 15% antimicrobial agent by weight, or 1% to 20% antimicrobial agent by weight.

The biguanide compound, if present, can comprise at least one of chlorhexidine (e.g., N,N''''1,6-Hexanediylbis[N'-(4-chlorophenyl)(imidodicarbonimidic diamide)]), alexidine (e.g., 1,1'-(1,6-Hexanediyl)bis{2-[N'-(2-ethylhexyl)carbamimidoyl]guanidine}), octenidine, (e.g., N-octyl-1-[10-(4-octyliminopyridin-1-yl)decyl]pyridin-4-imine), a polybiguanide such as Polyhexanide (polyhexamethylene biguanide), and a salt of any thereof.

The quaternary ammonium compound, if present, can comprise, for example, at least one of n-alkyl dimethyl benzyl ammonium chloride, didecyl dimethyl ammonium chloride, and n-alkyl dimethyl ethylbenzyl ammonium chloride, and various other suitable quaternary ammonium compounds as known in the art. The quaternary ammonium compound can comprise n-alkyl dimethyl benzyl ammonium chloride and didecyl dimethyl ammonium chloride. The quaternary ammonium compound may be BTC 1210 ®, available from Stepan Company, Northfield, Ill. BTC 1210 ® can comprise n-alkyl dimethyl benzyl ammonium chloride and didecyl dimethyl ammonium chloride.

The detergent composition can further comprise a hydrotrope. A hydrotrope is a substance that can solubilize hydrophobic substances while in aqueous solution. Hydrotropes generally do not form micelles as readily as surfactants because the hydrophobic moieties of hydrotropes are too small to do so. The hydrotrope can be, for example, an anionic, cationic, or nonionic hydrotrope. The hydrotrope can be inorganic or organic and can comprise surfactant activity. Organic solvents can be sulfonated to create a sulfonic acid, which can then be neutralized to create a hydrotrope salt. The hydrotrope can comprise at least one of an alkanoic acid (e.g., sulfonic acid, carboxylic acid), an aromatic sulfonic acid, an aromatic carboxylic acid, and a salt of any thereof. The salt of the alkanoic acid can be, for example, a sodium alkanoate salt. The hydrotrope can comprise a toluenesulfonyl functional group. The hydrotrope can comprise at least one of urea, p-toluenesulfonic acid (e.g., 4-methylbenzene-1-sulfonic acid), xylene sulfonic acid (e.g., 2,5-dimethylbenzenesulfonic acid), cumene sulfonic acid (e.g., 2(or 4)-(isopropyl)benzenesulphonic acid), and a salt of any thereof. If an anionic hydrotrope is employed, the hydrotrope can comprise at least one of Cola® Trope INC, Cola® Trope OD, and Cola® Trope CA. All three Cola® Trope substances are available from Colonial Chemical, Inc., South Pittsburgh, Tenn., USA. All three Cola® Trope substances comprise sodium alkanoate.

The hydrotrope can be present in the detergent compositions of the present disclosure in any effective amount. For example, the detergent compositions of the present disclosure can comprise at least 0.01% hydrotrope by weight based on the total weight of the detergent composition such as, for example, at least 0.1% hydrotrope by weight, at least 1% hydrotrope by weight, at least 5% hydrotrope by weight, at least 10% hydrotrope by weight, at least 15% hydrotrope by weight, at least 20% hydrotrope by weight, or at least 25% hydrotrope by weight. The detergent composition can comprise 30% or less hydrotrope by weight based on the total weight of the detergent composition such as, for example, 25% or less hydrotrope by weight, 20% or less hydrotrope by weight, 15% or less hydrotrope by weight, 10% or less hydrotrope by weight, 5% or less hydrotrope by weight, 1% or less hydrotrope by weight, or 0.1% or less hydrotrope by weight. The detergent composition can comprise 0.01% to 30% hydrotrope by weight based on the total weight of the detergent composition such as, for example, 0.1% to 30% hydrotrope by weight, 1% to 30% hydrotrope by weight, 5% to 20% hydrotrope by weight, 5% to 15% hydrotrope by weight, 10% to 20% hydrotrope by weight, or 10% to 15% hydrotrope by weight.

The detergent composition can further comprise an enzyme component. The enzyme component can be in the form of a liquid enzyme solution or a dry, powdered component (e.g., lyophilized). The enzyme can remove and/or eliminate debris via enzymatic digestion (e.g., decomposition) of the debris. The enzyme can comprise a hydrolase enzyme. The hydrolase enzyme can break chemical bonds in the debris and/or bioburden, by the addition of a water molecule (e.g., hydrolysis). For example, the hydrolase enzyme can remove and/or eliminate lipids, carbohydrates, proteins, peptides, and nucleic acids from an object. The hydrolase enzyme can comprise at least one of a lipase, a protease, a peptidase, an amylase, a glycosidase, a cellulase, a DNAse, and a nuclease. The enzyme can be selected based on a pH of a detergent composition and/or effectiveness on removing and/or eliminating a select debris and/or bioburden.

The enzyme can be present in the detergent compositions of the present disclosure in any effective amount. For example, the enzyme can comprise at least 0.001% active enzyme protein by weight based on the total dry weight of the enzyme such as, for example, at least 0.01% active enzyme protein, at least 0.1% active enzyme protein, at least 1% active enzyme protein, at least 5% active enzyme protein, at least 10% active enzyme protein, or at least 15% active enzyme protein. The enzyme can comprise 20% or less active enzyme protein by weight based on the total dry weight of the enzyme such as, for example, 15% or less active enzyme protein, 10% or less active enzyme protein, 5% or less active enzyme protein, 1% or less active enzyme protein, 0.1% or less active enzyme protein, or 0.01% or less active enzyme protein. The enzyme can comprise 0.001% to 20% active enzyme protein by weight based on the total dry weight of the enzyme such as, for example, 0.01% to 20% active enzyme protein, 0.1% to 20% active enzyme protein, 0.1% to 10% active enzyme protein, 1% to 10% active enzyme protein, or 1% to 5% active enzyme protein.

The pH the detergent composition can be adjusted based on the enzyme such that the enzyme has an enzymatic activity suitable to remove and/or eliminate debris and/or bioburden. For example, the detergent composition can have a pH of at least 6.0 such as, for example, at least 6.5, at least 7.0, at least 7.5, at least 8.0, at least 9, at least 10, or at least 11. The detergent composition can have a pH of less than 12 such as, for example, less than 11, less than 10, less than 9.0, less than 8, less than 7.5, less than 7.0, or less than 6.5. The detergent composition can have a pH in a range of 6 to 12 such as, for example, 6 to 8, 7 to 10, 7 to 9, or 8 to 11.

The pH of the detergent composition can be adjusted by adding a pH adjusting agent. The pH adjusting agent can be, for example, at least one of an acid and a base. The pH adjusting agent can comprise, for example, at least one of sodium hydroxide, potassium hydroxide, monoethanolamine, diethanolamine, and triethanolamine. The detergent composition can comprise any effective amount of pH adjusting agent to achieve the desired pH. For example, the detergent composition can comprise 2% or less of a pH adjusting agent based on the total weight of the detergent composition such as, for example, 1% or less of a pH adjusting agent, 0.5% or less of a pH adjusting agent, 0.1% or less of a pH adjusting agent, 0.01% or less of a pH adjusting agent, 0.001% or less of a pH adjusting agent. The detergent composition can comprise at least 0.0001% of a pH adjusting agent based on the total weight of the detergent composition such as, for example, at least 0.001% of a pH adjusting agent, at least 0.01% of a pH adjusting agent, at least 0.1% of a pH adjusting agent, at least 0.5% of a pH adjusting agent, or at least 1% of a pH adjusting agent. The detergent composition can comprise 0.0001% to 2% of a pH adjusting agent based on the total weight of the detergent composition such as, for example, 0.1% to 2% of a pH adjusting agent, 0.01% to 2% of a pH adjusting agent, or 0.001% to 1% of a pH adjusting agent.

Detergent compositions of the present disclosure can further comprise a boron-containing compound such as, for example, boric acid (e.g., $H_3BO_3$), borax (e.g., mineral salts of boric acid, including commercially provided, partially dehydrated salts), and other similar boron-containing compounds. These boron-containing compounds can improve the pH buffering, cleaning performance, and enzyme stability of a detergent composition. Surprisingly, however, it has been found that examples of the detergent compositions of the present disclosure do not require boron-containing compounds for aspects of their performance such as, for example, enzyme stability, pH buffering, and/or cleaning performance. Thus, it may be advantageous for the detergent compositions of the present disclosure to comprise a limited amount of a boron-containing compound, only incidental (i.e., trace) amounts of a boron-containing compound, no measurable boron-containing compound at all, or no intentionally added boron-containing compound. For example, detergent compositions of the present disclosure can comprise 0.1% or less by weight of a boron-containing compound based on the total weight of the detergent composition such as, for example, 0.01% or less by weight of a boron-containing compound, 0.001% or less by weight of a boron-containing compound, 0.0001% or less by weight of a boron-containing compound, or no measurable boron-containing compound.

The detergent composition of the present disclosure can further comprise a buffer component. The buffer can stabilize the pH of the detergent composition and can maintain a chemical environment that can be compatible with other components of the detergent composition such as, for example, the enzyme. The buffer can comprise, for example, a conjugate acid/base pair. The conjugate acid/base pair can comprise a zwitterion compound. The zwitterion compound can accept and donate hydrogen ions in response to pH changes, thereby maintaining a consistent pH. The zwitterion compound can comprise an amino acid, such as, for example, glycine. The conjugate acid/conjugate base pair can comprise, for example, at least one of tris(hydroxymethyl)aminomethane, a carbonate buffer, and a phosphate buffer. If present, the buffer may be present in the detergent compositions of the present disclosure in any effective amount. For example, the detergent composition can comprise 10% or less by weight of buffer based on the total weight of the detergent composition such as, for example, 5% or less buffer by weight, 3% or less buffer by weight, 1% or less buffer by weight, 0.5% or less buffer by weight, 0.1% or less buffer by weight, 0.01% or less buffer by weight, or 0.001% or less buffer by weight. The detergent compositions of the present disclosure can comprise at least 0.0001% by weight of buffer based on the total weight of the detergent composition such as, for example, at least 0.001% by weight of buffer, at least 0.01% by weight of buffer, at least 0.1% by weight of buffer, at least 0.5% by weight of buffer, at least 1% by weight of buffer, at least 3% buffer by weight, or at least 5% by weight of buffer. The detergent compositions of the present disclosure can comprise 0.0001% to 10% by weight of buffer based on the total weight of the detergent composition such as, for example, 0.001% to 5% by weight of buffer, 0.01% to 5% by weight of buffer, 0.1% to 5% by weight of buffer, 0.5% to 3% by weight of buffer, or 0.5% to 2% by weight of buffer.

The detergent composition of the present disclosure can further comprise a solvent. The solvent can assist in removing and/or eliminating debris from the object. The solvent can enhance solubility of the components of the detergent composition and/or the solubility of the debris and/or bioburden. Enhancing the solubility of the debris and/or bioburden can facilitate removal and/or elimination of the debris and/or bioburden. The solvent can comprise, for example, at least one of a glycol ether, propylene glycol, ethylene glycol, methanol, ethanol, isopropanol, and n-propanol. The glycol ether can comprise, for example, at least one of 2-ethoxyethanol, 2-butoxyethanol, methyl ether, and propylene glycol n-butyl ether. If present, the solvent may be present in the detergent compositions of the present disclosure in any effective amount. For example, the detergent composition can comprise at least 0.01% solvent by weight based on the total weight of the detergent composition such as, for example, at least 0.1% solvent by weight, at least 1% solvent by weight, at least 5% solvent by weight, at least 10% solvent by weight, at least 11% solvent by weight, at least 12% solvent by weight, at least 13% solvent by weight, at least 14% solvent by weight, at least 15% solvent by weight, at least 20% solvent by weight, at least 30% solvent by weight, or at least 40% solvent by weight. The detergent composition can comprise 50% or less solvent by weight based on the total weight of the detergent composition such as, for example, 40% or less solvent by weight, 30% or less solvent by weight, 20% or less solvent by weight, 15% or less solvent by weight, 14% or less solvent by weight, 13% or less solvent by weight, 12% or less solvent by weight, 11% or less solvent by weight, 10% or less solvent by weight, 5% or less solvent by weight, 1% or less solvent by weight, or 0.1% or less solvent by weight. The detergent composition can comprise 0.01% to 50% solvent by weight based on the total weight of the detergent composition such as, for example, 0.1% to 5% solvent by weight, 5% to 20% solvent by weight, 10% to 20% solvent by weight, or 10% to 15% solvent by weight.

The detergent compositions of the present disclosure can further comprise a salt. The salt can increase removal and/or elimination of debris by the enzyme. The salt can act as an enzyme stabilizer. The salt can be organic or inorganic and can comprise, for example, at least one of calcium chloride, potassium chloride, sodium chloride, sodium citrate, and magnesium chloride. If present, the salt may be present in the detergent compositions of the present disclosure in any effective amount. For example, the detergent composition can comprise 10% or less of salt by weight, based on the total weight of the detergent composition such as, for example, 5% or less salt by weight, 4% or less salt by weight, 3% or less salt by weight, 2% or less salt by weight, 1% or less salt by weight, 0.5% or less salt by weight, 0.1% or less salt by weight, or 0.01% or less salt by weight. The detergent composition can comprise at least 0.001% of salt by weight, based on the total weight of the detergent composition such as, for example, at least 0.01% of salt by weight, at least 0.1% of salt by weight, at least 0.5% of salt by weight, at least 1% of salt by weight, at least 2% of salt by weight, at least 3% of salt by weight, at least 4% of salt by weight, or at least 5% of salt by weight. The detergent composition can comprise 0.001% to 10% of salt by weight, based on the total weight of the detergent composition such as, for example, 0.1% to 5% of salt by weight or 0.001% to 0.1%.

The detergent composition of the present disclosure can further comprise a chelating agent. The chelating agent can increase cleaning by the detergent composition. For example, the chelating agent can chelate a metal ion and/or chelate at the pH of the detergent composition. The chelating agent can be a non-phosphate chelator and/or can be biodegradable. The chelating agent can comprise, for example, at least one of, methylglycindiacetic acid, N,N-bis(carboxymethyl)-L-glutamic acid, citric acid, a gluconic acid, N-(1,2-dicarboxyethyl)aspartic acid, ethylenediamine-N, N'-disuccinic acid, and a salt of any thereof. The chelating agent can comprise Trilon M®, available from BASF, SE, Ludwigshafen, Germany. Trilon M® can comprise trisodium salt of methylglycindiacetic acid. The chelating agent can comprise Dissolvine® GL-47-S, available from Akzo Nobel N.V., Amsterdam, Netherlands. Dissolvine® GL-47-S can comprise Tetrasodium N,N-bis(carboxymethyl)-L-glutamate. The chelating agent can comprise Baypure® CX100, available from Lanxess AG, Cologne, Germany. Baypure® CX100 can comprise N-(1,2-dicarboxyethyl)aspartic acid as a sodium salt (e.g., Tetrasodium iminodisuccinate).

If present, the chelating agent may be present in the detergent compositions of the present disclosure in any effective amount. For example, the detergent composition can comprise 5% or less of chelating agent by weight based on the total weight of the detergent composition such as, for example, 4% or less of chelating agent by weight, 3% or less of chelating agent by weight, 2% or less of chelating agent by weight, 1% or less of chelating agent by weight, 0.1% or less of chelating agent by weight, or 0.01% or less of chelating agent by weight. The detergent composition can comprise at least 0.005% of chelating agent by weight based on the total weight of the detergent composition such as, for example, at least 0.01% of chelating agent by weight, at least 0.1% of chelating agent by weight, at least 1% of chelating agent by weight, at least 2% of chelating agent by weight, at least 3% of chelating agent by weight, or at least 4% of chelating agent by weight. The detergent composition can comprise 0.005% to 5% of chelating agent by weight based on the total weight of the detergent composition such as, for example, 0.005% to 0.1% of chelating agent by weight, 0.5% to 3% of chelating agent by weight, 1% to 3% of chelating agent by weight.

The detergent composition of the present disclosure can comprise surfactants in addition to the hydrotrope, such as, for example, a non-ionic surfactant. The non-ionic surfactant can increase the solubility of debris and/or bioburden, and aid in the removal of the debris and/or bioburden from the object. The non-ionic surfactant can be low foaming. Non-ionic surfactants can comprise, for example, at least one of a fatty alcohol ethylene oxide/propylene oxide copolymer derivative, a polyoxyethylene-polyoxypropylene block copolymer, and various other non-ionic surfactants as known in the art. The non-ionic surfactant may be Dehypon® LS 54 available from BASF SE, Ludwigshafen, Germany. Dehypon® LS 54 can comprise a C12-15 fatty alcohol ethylene oxide/propylene oxide copolymer derivative. The non-ionic surfactant may be Dehypon® LS 36 available from BASF SE, Ludwigshafen, Germany. Dehypon® LS 36 can comprise a C12-14 fatty alcohol ethylene oxide/propylene oxide copolymer derivative. The non-ionic surfactant may be Pluronic® L62 available from BASF SE, Ludwigshafen, Germany. Pluronic® L62 can comprise a polyoxyethylene-polyoxypropylene block copolymer.

If present, the non-ionic surfactant may be present in the detergent compositions of the present disclosure in any effective amount. For example, the detergent composition can comprise at least 0.005% of non-ionic surfactant by weight based on the total weight of the detergent composition such as, for example, at least 0.01% of non-ionic surfactant by weight, at least 0.1% of non-ionic surfactant by weight, at least 1% of non-ionic surfactant by weight, at least 2% of non-ionic surfactant by weight, at least 3% of non-ionic surfactant by weight, at least 4% of non-ionic surfactant by weight, at least 5% of non-ionic surfactant by weight, at least 6% of non-ionic surfactant by weight, or at least 7% of non-ionic surfactant by weight. The detergent composition can comprise 10% or less of non-ionic surfactant by weight based on the total weight of the detergent composition such as, for example, 7% or less of non-ionic surfactant by weight, 6% or less of non-ionic surfactant by weight, 5% or less of non-ionic surfactant by weight, 4% or less of non-ionic surfactant by weight, 3% or less of non-ionic surfactant by weight, 2% or less of non-ionic surfactant by weight, 1% or less of non-ionic surfactant by weight, 0.1% or less of non-ionic surfactant by weight, or 0.01% or less of non-ionic surfactant by weight. The detergent composition can comprise 0.005% to 10% of non-ionic surfactant by weight based on the total weight of the detergent composition such as, for example, 0.01% to 1% of non-ionic surfactant by weight, 0.5% to 7% of non-ionic surfactant by weight, 0.5% to 6% of non-ionic surfactant by weight, 1% to 6% of non-ionic surfactant by weight, or 2% to 6% of non-ionic surfactant by weight.

The detergent compositions of the present disclosure can further comprise at least 10% by weight of water based on the total weight of the detergent composition such as, for example, at least 25% water by weight, at least 35% water by weight, at least 40% water by weight, at least 45% water by weight, at least 50% water by weight, at least 55% water by weight, or at least 60% water by weight. The water content of the detergent composition can be in a range of 20% to 60% by weight based on the total weight of the detergent composition such as, for example, 25% to 55% by weight, 30% to 55% by weight, or 34% to 50% water by weight. The water employed can be any suitable type of water known in the art such as, for example, at least one of de-ionized water, distilled water, reverse osmosis treated water, filtered water, sterile water, tap water, and the like.

It is understood that a detergent composition of the present disclosure can be made in a concentrated or diluted form. Accordingly, the present disclosure provides examples wherein the percentage by weight, based on the total weight of the composition, of various components of the detergent composition are at relatively high values, and examples wherein the percentage by weight, based on the total weight of the composition, of various components of the detergent composition are at relatively low values. Compositions of relatively high and relatively low concentrations are contemplated herein and may serve certain intended purposes.

The detergent compositions of the present disclosure can be stored for a period of time before use in a cleaning and/or disinfecting. After storage, the detergent compositions can maintain an enzymatic activity of an enzyme suitable for removing and/or eliminating debris and/or bioburden. For example, the detergent compositions of the present disclosure can comprise a four week storage stability at 40 degrees Celsius suitable to maintain the enzymatic activity of the enzyme of at least 40% of an initial enzymatic activity of the enzyme prior to storage such as, for example, at least 50% of the initial enzymatic activity, at least 60% of the initial enzymatic activity, at least 70% of the initial enzymatic activity, at least 80% of the initial enzymatic activity, at least 90% of the initial enzymatic activity, or at least 95% of the initial enzymatic activity prior to storage. The detergent compositions of the present disclosure can comprise a four week storage stability at 30 degrees Celsius suitable to maintain an enzymatic activity of the enzyme of at least 40% of an initial enzymatic activity of the enzyme prior to storage such as, for example, at least 50% of the initial enzymatic activity, at least 60% of the initial enzymatic activity, at least 70% of the initial enzymatic activity, at least 80% of the initial enzymatic activity, at least 90% of the initial enzymatic activity, or at least 95% of the initial enzymatic activity. The detergent compositions of the present disclosure can comprise a four week storage stability at 25 degrees Celsius suitable to maintain an enzymatic activity of the enzyme of at least 40% of an initial enzymatic activity of the enzyme in the enzyme prior to storage such as, for example, at least 50% of the initial enzymatic activity, at least 60% of the initial enzymatic activity, at least 70% of the initial enzymatic activity, at least 80% of the initial enzymatic activity, at least 90% of the initial enzymatic activity, or at least 95% of the initial enzymatic activity.

The present disclosure also provides methods of making a detergent composition. The components of the detergent composition set forth herein can be combined in any suitable manner and in the various amounts set forth herein. For example, the antimicrobial agent, the hydrotrope, and the enzyme can be combined in any manner in the amounts set forth herein to form the detergent compositions of the present disclosure. For example, based on the total weight of the detergent composition, at least 10% by weight of water, at least 0.001% by weight of the antimicrobial agent, at least 0.01% by weight of the hydrotrope, and the enzyme can be combined to form the detergent composition. The components of the detergent compositions of the present disclosure can be combined in any order. For example, combining the water, antimicrobial agent, and the hydrotrope can occur prior to adding the enzyme. Also, optional components provided herein can be added to the detergent compositions of the present disclosure. For example, at least one of the buffer, the chelating agent, the solvent, the non-ionic surfactant, and the salt described herein can be added to the detergent compositions of the present disclosure. The pH of the detergent composition can be adjusted to a pH suitable to maintain enzymatic activity of an enzyme. The pH can be adjusted prior to adding the enzyme. When a dry, powdered detergent composition is desired, dry, powered components can be mixed together to form a powdered mixture and then surfactants can be mixed with, such as sprayed onto (e.g., in a liquid form), the powdered mixture. The powdered mixture can be mixed until a desired homogeneity is achieved.

The components of the detergent compositions of the present disclosure can be combined in various orders. For example, the components of the detergent composition can be combined by adding each component one at a time, adding multiple components in a single step, or adding a portion of a component at multiple addition stages. For example, based on the total weight of the detergent composition, at least 10% by weight of water can be combined with at least 0.001% by weight of the antimicrobial agent, followed by at least 0.01% by weight of the hydrotrope. The buffer, if present, can then be added, followed by the addition of the enzyme. Thereafter, the pH can be adjusted to a level appropriate for the enzyme to retain enzymatic activity. Alternatively, the enzyme can be added after the pH of the detergent composition has been adjusted.

The water, the antimicrobial agent, the hydrotrope, the non-ionic surfactant, and the buffer can each be added in a single portion or in multiple portions. For example, a first portion of the buffer can be added to the water to form a first composition, the solvent can be added to the first composition to form a second composition, and the remaining portion of the buffer can be added to the second composition to form a third composition. Then, the third composition can be combined with the antimicrobial agent, the hydrotrope, and the enzyme, in a single step, in series, or in some other combination, to form the detergent composition of the present disclosure. The enzyme can be the final component added.

A method for cleaning all or a portion of an object is also provided herein. For example, the object can be a reusable medical device such as, for example, an endoscope, and the detergent composition can be used to clean and disinfect the endoscope. The detergent composition of the present disclosure can clean and/or disinfect the object by removing debris and/or bioburden, from the object. The method for cleaning the object can comprise applying the detergent composition of the present disclosure to the object. As used herein, "applying" is meant to include all or a portion of the object, including one or more surfaces of the object, whether the surface of the object is an exterior surface, an interior surface, or a cavity of the object. As set forth above, the detergent composition can comprise the various components and amounts set forth herein. For example, based on the total weight of the detergent composition, the detergent composition can comprise at least 0.001% by weight of the antimicrobial agent, at least 0.01% by weight of the hydrotrope, and the enzyme. Application of the detergent composition of the present disclosure thereby cleans the object. The detergent composition can be applied to the object by any suitable means. For example, applying the detergent composition of the present disclosure to the object can comprise at least one of depositing, scrubbing, spraying, rolling, submerging, and/or agitating the detergent composition over, onto, or inside the object.

Before or during applying the detergent composition of the present disclosure to the object, the detergent composition can be diluted, if necessary, to a lower concentration. The dilution can be by a factor of at least 5-fold, at least 10-fold, at least 20-fold, at least 50-fold, at least 100-fold, at least 200-fold, or any factor appropriate to achieve treatment of the object and/or conserve the detergent composition. The diluting can be automated or manual. The diluent can comprise or consist of, for example, water in any type as already described herein.

The detergent composition can be applied to the object manually or automatically (e.g., mechanically) to clean and/or disinfect the object. After application, the detergent composition can be immediately removed from, or be allowed to remain on, the object for a period of time. The detergent composition and any remaining debris or bioburden can be removed from the object by wiping, rinsing, drying, or combinations thereof.

The cleaning and/or disinfecting can occur in a treatment system such as, for example, an automated endoscope re-processor. Referring to FIG. 1, the treatment system 100 can comprise a chamber 102 including a basin 104 in fluid communication with a reservoir 106. The chamber 102 may be any suitable size and configuration to receive the object (not shown), and can be suitable to perform a treatment process on the object. The chamber 102 can be at least one of a cleaning chamber and/or a disinfection chamber. The object can comprise an endoscope. The treatment system 100 can comprise an automated endoscope re-processor.

The reservoir 106 can be any suitable size and configuration to receive the detergent composition of the present disclosure and can store the detergent composition until the detergent composition can be output into the basin 104. The basin 104 can be in fluid communication with the reservoir 106 via a treatment line 108 and can receive detergent composition from the reservoir 106. The treatment line 108 can receive the detergent composition from the reservoir 106 and transport the detergent composition to the basin 104. The treatment line 108 can include at least one of a tube, a valve, and a pump. The treatment line 108 can control the amount of detergent composition provided to the basin 104. For example, the detergent composition can be metered into the basin 104 by the treatment line 108 until a select amount of detergent composition has been provided to the basin 104. The basin 104 can be in fluid communication with a drain line 110 to remove detergent composition from the basin.

An object to be treated can be provided to the chamber 102 and subjected to the treatment process therein. The treatment process can comprise providing the detergent composition to the basin 104 and/or applying the detergent composition to the object. For example, the detergent composition can be sprayed and/or deposited on the object by a spray arm (not shown) in the chamber 102. Thereafter, the object can be optionally wiped, rinsed, and/or dried and removed from the chamber 102.

Applying the detergent composition to the object can occur at an operating temperature in a range of 15° C. to 60° C. such as, for example, 15° C. to 50° C., 30° C. to 50° C., or 43° C. to 48° C. The operating temperature can be achieved through automation, such as in an automated endoscope re-processor, a similar machine, or by heating the detergent composition independent of an automated endoscope re-processor.

EXAMPLES

The present disclosure will be more fully understood by reference to the following examples, which provide illustrative, non-limiting aspects of the invention. The examples describe the making of detergent compositions and use thereof in cleaning and/or disinfecting.

Example 1

Detergent compositions F1-F6*, provided below, were manufactured as shown in Table 1. Glycine and calcium chloride were obtained from VWR International, Randor, Pa. Sodium hydroxide and 2-ethoxyethanol were obtained from Sigma-Aldrich, St. Louis, Mo. Propylene glycol was obtained from Ward's Science, Rochester, N.Y. Savinase® everis, Stainzyme® plus, and Lipex® everis were obtained from Novozymes A/S, Denmark. Savinase® everis comprises an alkaline protease having an active enzyme protein of 2.5% to 5% by weight of the Savinase® solution. Stainzyme® plus comprises an alpha-amylase having active enzyme protein of 1% to 2.5% by weight of the Stainzyme® solution. Lipex® everis comprises a lipase. Savinase® everis, Stainzyme® plus, and Lipex® everis were obtained in solution. BTC 1210 ® was obtained from Stepan Company, Northfield, Ill. Trilon M® was obtained from BASF, SE, Ludwigshafen, Germany. Dehypon® LS 54 was obtained from BASF SE, Ludwigshafen, Germany.

1.6 kilograms of each detergent composition F1-F6* was prepared. For the preparation of each detergent compositions F1-F6*, glycine was added to de-ionized water and then sodium hydroxide and Trilon M® were added in order respectively. The pH of the detergent composition was adjusted and/or maintained by addition of the glycine and the sodium hydroxide to the detergent composition. If used (e.g., detergent compositions F1, F3, F4*, and F6*), 2-ethoxyethanol was added after the addition of the Trilon M®. Similarly, if used (detergent compositions F2, F3, F5*, and F6*), propylene glycol was added after the addition of the Trilon M® and the optional addition of the 2-ethoxyethanol. Then, for detergent compositions F4*-F6*, BTC® 1210 was added. Thereafter, for detergent compositions F1-F6*, Dehypon® LS 54 and Calcium chloride were added in order respectively. The enzyme solutions, Savinase® everis, Stainzyme® plus, and Lipex® everis were added last.

As shown in Table 1, detergent compositions F1 and F4* are similar except that F4* comprises BTC® 1210. Detergent compositions F2 and F5* are similar except that F5* comprises BTC® 1210. Detergent compositions F3 and F6* are similar except that F6* comprises BTC® 1210.

TABLE 1

Weight percentage (wt. %) of each component of the detergent compositions F1-F6* based on the total weight of the composition.

| Component | Detergent Composition | | | | | |
| --- | --- | --- | --- | --- | --- | --- |
| | F1 | F4* | F2 | F5* | F3 | F6* |
| De-ionized Water (wt. %) | 49.84 | 44.842 | 49.842 | 44.842 | 39.842 | 34.842 |
| Glycine (wt. %) | 2 | 2 | 2 | 2 | 2 | 2 |
| Sodium Hydroxide (wt. %) | 0.098 | 0.098 | 0.098 | 0.098 | 0.098 | 0.098 |
| Trilon M ® (wt. %) | 1 | 1 | 1 | 1 | 1 | 1 |
| 2-Ethoxyethanol (wt. %) | 25 | 25 | — | — | 25 | 25 |
| Propylene glycol (wt. %) | — | — | 25 | 25 | 10 | 10 |
| BTC ® 1210 (wt. %) | — | 5 | — | 5 | — | 5 |
| Dehypon ® LS 54 (wt. %) | 2 | 2 | 2 | 2 | 2 | 2 |
| Calcium chloride (wt. %) | 0.06 | 0.06 | 0.06 | 0.06 | 0.06 | 0.06 |

TABLE 1-continued

Weight percentage (wt. %) of each component of the detergent compositions F1-F6* based on the total weight of the composition.

| Component | Detergent Composition | | | | | |
|---|---|---|---|---|---|---|
| | F1 | F4* | F2 | F5* | F3 | F6* |
| Savinase ® everis (wt. %) | 10 | 10 | 10 | 10 | 10 | 10 |
| Stainzyme ® plus (wt. %) | 5 | 5 | 5 | 5 | 5 | 5 |
| Lipex ® everis (wt. %) | 5 | 5 | 5 | 5 | 5 | 5 |
| Final pH | 8.99 | 8.77 | 8.95 | 8.86 | 8.98 | 8.85 |

*These detergent compositions contain a quaternary ammonium compound.

Example 2

To determine the effects of quaternary ammonium compound presence on enzymatic activity, the detergent compositions F1-F6* were stored at 25 degrees Celsius, 30 degrees Celsius, 40 degrees Celsius, and 50 degrees Celsius in duplicate for 4 weeks. At two weeks and four weeks, aliquots of the stored detergent compositions F1-F6* were sampled and tested for the enzymatic activity against a standard substrate. Enzyme activities of each aliquot were compared to initial activities of the detergent compositions F1-F6* before storage. Surprisingly, as illustrated in Tables 2-7 and described herein, the detergent compositions F4*-F6* maintained an amount of enzymatic activity suitable to remove and/or eliminate debris and/or bioburden from an object after storage.

Results for Savinase® evens are shown in Table 2 which shows enzymatic activity data after 2 weeks of storage and Table 3 which shows enzymatic activity data after 4 weeks of storage. Detergent compositions F4*-F6* maintained an amount of Savinase® enzyme activity suitable to clean and/or disinfect an object after storage for 4 weeks at 25 degrees Celsius, 30 degrees Celsius, and 40 degrees Celsius. Detergent composition F5* had an enhanced Savinase® storage stability compared to detergent composition F2 after storage for 4 weeks at 25 degrees Celsius, 30 degrees Celsius, and 40 degrees Celsius.

TABLE 2

Savinase ® enzymatic activity as a percentage of initial enzymatic activity after 2 weeks of storage

| Storage Temperature | Detergent Composition | | | | | |
|---|---|---|---|---|---|---|
| | F1 | F4* | F2 | F5* | F3 | F6* |
| 25° C. | 100 | 89 | 92 | 96 | 96 | 92 |
| | 95 | 89 | 89 | 96 | 97 | 96 |
| 30° C. | 87 | 73 | 86 | 97 | 85 | 80 |
| | 86 | 72 | 88 | 94 | 84 | 84 |
| 40° C. | 55 | 39 | 76 | 77 | 48 | 41 |
| | 55 | 42 | 70 | 79 | 49 | 40 |

TABLE 3

Savinase ® enzymatic activity as a percentage of initial enzymatic activity after 4 weeks of storage

| Storage Temperature | Detergent Composition | | | | | |
|---|---|---|---|---|---|---|
| | F1 | F4* | F2 | F5* | F3 | F6* |
| 25° C. | 93 | 84 | 90 | 97 | 94 | 90 |
| | 92 | 82 | 89 | 100 | 92 | 97 |
| 30° C. | 74 | 63 | 87 | 94 | 71 | 73 |
| | 79 | 64 | 87 | 100 | 71 | 72 |
| 40° C. | 37 | 23 | 56 | 70 | 37 | 21 |
| | 37 | 23 | 56 | 68 | 34 | 22 |

Results for Stainzyme® Plus are shown in Table 4 which shows enzymatic activity data after 2 weeks of storage and Table 5 which shows enzymatic activity data after 4 weeks of storage. Detergent compositions F4*-F6* maintained an amount of Stainzyme® Plus enzymatic activity suitable to clean and/or disinfect an object after 4 weeks of storage at 25 degrees Celsius, 30 degrees Celsius, and 40 degrees Celsius. Detergent composition F5* had an enhanced Stainzyme® Plus storage stability compared to detergent composition F2 after 4 weeks of storage at 40 degrees Celsius. Detergent composition F6* had an enhanced Stainzyme® Plus storage stability compared to detergent composition F3 after 4 weeks of storage at 25 degrees Celsius, and 30 degrees Celsius, 40 degrees Celsius.

TABLE 4

Stainzyme ® Plus enzymatic activity as a percentage of initial enzymatic activity at 2 weeks

| Storage Temperature | Detergent Composition | | | | | |
|---|---|---|---|---|---|---|
| | F1 | F4* | F2 | F5* | F3 | F6* |
| 25° C. | 90 | 98 | 98 | 85 | 96 | 100 |
| | 89 | 97 | 95 | 89 | 96 | 100 |
| 30° C. | 85 | 96 | 91 | 87 | 94 | 100 |
| | 84 | 97 | 93 | 84 | 94 | 100 |
| 40° C. | 68 | 80 | 76 | 82 | 78 | 99 |
| | 67 | 84 | 78 | 80 | 76 | 97 |
| 50° C. | 63 | 74 | 50 | 73 | 16 | 86 |
| | 62 | 74 | 50 | 71 | 16 | 85 |

TABLE 5

Stainzyme ® Plus enzymatic activity as a percentage of initial enzymatic activity at 4 weeks

| Storage Temperature | Detergent Composition | | | | | |
|---|---|---|---|---|---|---|
| | F1 | F4* | F2 | F5* | F3 | F6* |
| 25° C. | 85 | 96 | 92 | 88 | 93 | 100 |
| | 82 | 95 | 93 | 88 | 93 | 100 |
| 30° C. | 76 | 93 | 83 | 84 | 86 | 100 |
| | 75 | 93 | 83 | 84 | 85 | 99 |
| 40° C. | 48 | 67 | 58 | 71 | 14 | 81 |
| | 49 | 65 | 61 | 72 | 14 | 83 |
| 50° C. | 47 | 60 | 40 | 61 | 14 | 72 |
| | 47 | 60 | 38 | 61 | 14 | 72 |

Example 3

Detergent compositions A1-A4, provided below, were manufactured as shown in Table 6. Glycine and calcium chloride were obtained from VWR International, Randor, Pa. Sodium hydroxide was obtained from Sigma-Aldrich, St. Louis, Mo. Propylene glycol was obtained from Ward's Science, Rochester, N.Y. Ethylene glycol was obtained from VWR International, Randor, Pa. Colatrope® OD was obtained from Colonial Chemical, Inc., South Pittsburgh, Tenn., USA. Dehypon® LS 54, Dehypon® LS 36, Pluronic® L62, and Trilon M® were obtained from BASF SE, Ludwigshafen, Germany. Baypure® CX100 was obtained from Lanxess AG, Cologne, Germany. Dissolvine® GLS 47 was obtained from Akzo Nobel N.V., Amsterdam, Netherlands.

1 kilogram of each detergent composition A1-A4 was prepared.

Example 4

To determine the cleaning efficacy of detergent compositions of the present disclosure, formulation A0 according to the present disclosure and as described in Example 3, was compared to commercially available detergent compositions, C1-C6, which are not according to the present disclosure. Each detergent composition (A0 and C1-C6) was tested with and without addition of an antimicrobial agent to control for the presence of an antimicrobial agent, which is not necessarily present in the commercially available detergent compositions. For all detergent compositions the antimicrobial agent was 5% by weight chlorhexidine gluconate (abbreviated as CHG), based on the total weight of the composition.

Detergent composition C1 is a commercially available neutral detergent composition comprising nonionic surfactants and triethanolamine. Detergent composition C2 is a commercially available enzymatic detergent composition comprising protease, amylase, and lipase enzymes. Detergent composition C3 is a commercially available enzymatic detergent composition comprising subtilisin protease. Detergent composition C4 is a commercially available detergent composition comprising an antimicrobial agent (a biguanide). Detergent composition C5 is a commercially available enzymatic detergent comprising subtilisins (protease enzyme). Detergent composition C6 is a commercially available dual enzymatic detergent comprising proteinase subtilisin and subtilisin (protease enzyme).

Cleaning efficacy was tested using stainless steel and plastic coupons. The stainless steel coupons were Tosi® coupons available from Healthmark Industries Company, Inc., Fraser Mich., USA. Each Tosi® coupon comprises a stainless steel plate treated with simulated blood test soil to

TABLE 6

Weight percentage (wt. %) of each component of the detergent compositions A1-A4 based on the total weight of the composition

| Component | Component Type | Detergent Compositions | | | | |
|---|---|---|---|---|---|---|
| | | A0 | A1 | A2 | A3 | A4 |
| De-ionized water | Solvent | Qs to 100 | Qs to 100 | Qs to 100 | Qs to 100 | Qs to 100 |
| Propylene glycol | Solvent | 20 | 10 | 12 | 15 | 0 |
| Ethylene glycol | Solvent | 0 | 0 | 0 | 0 | 15 |
| Sodium xylene sulfonate | Hydrotrope | 0 | 10 | 0 | 0 | 12 |
| Sodium cumene sulfonate | Hydrotrope | 0 | 0 | 0 | 10 | 0 |
| Colatrope ® OD | Hydrotrope | 15 | 0 | 15 | 0 | 0 |
| Calcium chloride | Enzyme stabilizer | 0.05 | 0.03 | 0.1 | 0.2 | 0.05 |
| Sodium citrate | Enzyme stabilizer | 1 | 0.5 | 1.5 | 3 | 2 |
| Sodium gluconate | Chelating agent | 1 | 2 | 0 | 0 | 0.7 |
| Trilon ® M | Chelating agent | 0 | 0 | 1 | 0 | 0 |
| Baypure ® CXI00 | Chelating agent | 0 | 0 | 0 | 2 | 0 |
| Dissolvine ® GLS 47 | Chelating agent | 1 | 0 | 0 | 0 | 1.5 |
| Dehypon ® LS 54 | Nonionic surfactant | 3 | 5 | 0 | 0 | 4 |
| Dehypon ® LS 36 | Nonionic surfactant | 0 | 0 | 2 | 0 | 1 |
| Pluronic ® L62 | Nonionic surfactant | 0 | 0 | 0 | 3 | 0.5 |
| Glycine | pH buffer | 1.2 | 1 | 1.2 | 0.8 | 2 |
| Amplify 100L | Amylase enzyme | 3 | 1 | 2 | 10 | 8 |
| Everis DUO 100L | Protease enzyme | 5 | 1 | 1.5 | 7 | 15 |
| Chlorohexidine (20% w/w solution in water) | Antimicrobial agent | 5 | 2 | 3 | 7 | 9 |
| Sodium hydroxide | pH adjuster | Up to pH = 9 | Up to pH = 8 | Up to pH = 9 | Up to pH = 10 | Up to pH = 11 |
| pH | | 9 | 8 | 9 | 10 | 11 | create a surface appropriate to test for cleaning activity. The simulated blood comprises blood proteins in a sodium chloride and calcium chloride solution. The plastic coupons were Verify® All Clean coupons available from STEMS Corporation Mentor, Ohio, USA. Each Verify® All Clean coupon comprises a plastic plate treated with a test soil comprising proteins, lipids, and polysaccharides. Thus, testing was conducted for cleaning of both metal and plastic surfaces, with and without antimicrobial agent.

The following procedure was used to perform the cleaning tests. First, each detergent composition was diluted with 200 PPM hard water to the recommended concentration in a first beaker. For detergent composition A0, the dilution factor was 1:100. Then, the resulting diluted detergent composition was heated to 45° C. Then, a plastic and stainless steel coupon were immersed in the beaker for 10 min. After 10 min, each coupon was removed, and rinsed with de-ionized water. Then, each coupon was dried at room temperature overnight and examined and photographed for cleaning efficacy.

Results are shown in FIGS. 2-8. Generally, each Figure has a panel A, B, C, and D, with one photograph in each panel. Panel A of each Figure shows a stainless steel coupon treated with a diluted detergent composition to which 5% CHG was added. Panel B of each Figure shows a plastic coupon treated with a diluted detergent composition to which 5% CHG was added. Panel C of each Figure shows a stainless steel coupon treated with a diluted detergent composition to which no CHG was added. Panel D of each Figure shows a plastic coupon treated with a diluted detergent composition to which no CHG was added.

FIG. 2 shows photographs of stainless steel and plastic coupons that were treated with diluted detergent composition A0. Panel 2A shows a stainless steel coupon treated with diluted detergent composition A0 to which 5% CHG was added. Panel 2B shows a plastic coupon treated with diluted detergent composition A0 to which 5% CHG was added. Panel 2C shows a stainless steel coupon treated with diluted detergent composition A0 to which no CHG was added. Panel 2D shows a plastic coupon treated with diluted detergent composition A0 to which no CHG was added.

FIG. 3 shows photographs of stainless steel and plastic coupons that were treated with diluted detergent composition C1. Panel 3A shows a stainless steel coupon treated with diluted detergent composition C1 to which 5% CHG was added. Panel 3B shows a plastic coupon treated with diluted detergent composition C1 to which 5% CHG was added. Panel 3C shows a stainless steel coupon treated with diluted detergent composition C1 to which no CHG was added. Panel 3D shows a plastic coupon treated with diluted detergent composition C1 to which no CHG was added. For all panels A-D of FIG. 3, comparison to the corresponding panels of FIG. 2 shows that cleaning efficacy is increased in detergent compositions of the present disclosure, based on increased removal of test soil in FIG. 2.

FIG. 4 shows photographs of stainless steel and plastic coupons that were treated with diluted detergent composition C2. Data for panels 4A and B was not obtainable because the 5% CHG that was added to detergent composition C2 was insoluble. Panel 4C shows a stainless steel coupon treated with diluted detergent composition C2 to which no CHG was added. Panel 4D shows a plastic coupon treated with diluted detergent composition C2 to which no CHG was added. For panels C and D of FIG. 4, comparison to the corresponding panels of FIG. 2 shows that cleaning efficacy is increased in detergent compositions of the present disclosure, based on increased removal of test soil in FIG. 2.

FIG. 5 shows photographs of stainless steel and plastic coupons that were treated with diluted detergent composition C3. Data for panels 5A and B was not obtainable because the 5% CHG that was added to detergent composition C3 was insoluble. Panel 5C shows a stainless steel coupon treated with diluted detergent composition C3 to which no CHG was added. Panel 5D shows a plastic coupon treated with diluted detergent composition C3 to which no CHG was added. For panels C and D of FIG. 5, comparison to the corresponding panels of FIG. 2 shows that cleaning efficacy is increased in detergent compositions of the present disclosure, based on increased removal of test soil in FIG. 2.

FIG. 6 shows photographs of stainless steel and plastic coupons that were treated with diluted detergent composition C4. Panel 6A shows a stainless steel coupon treated with diluted detergent composition C4 to which 5% CHG was added. Panel 6B shows a plastic coupon treated with diluted detergent composition C4 to which 5% CHG was added. Panel 6C shows a stainless steel coupon treated with diluted detergent composition C4 to which no CHG was added. Panel 6D shows a plastic coupon treated with diluted detergent composition C4 to which no CHG was added. For all panels A-D of FIG. 6, comparison to the corresponding panels of FIG. 2 shows that cleaning efficacy is increased in detergent compositions of the present disclosure, based on increased removal of test soil in FIG. 2.

FIG. 7 shows photographs of stainless steel and plastic coupons that were treated with diluted detergent composition C5. Panel 7A shows a stainless steel coupon treated with diluted detergent composition C5 to which 5% CHG was added. Panel 7B shows a plastic coupon treated with diluted detergent composition C5 to which 5% CHG was added. Panel 7C shows a stainless steel coupon treated with diluted detergent composition C5 to which no CHG was added. Panel 7D shows a plastic coupon treated with diluted detergent composition C5 to which no CHG was added. For all panels A-D of FIG. 7, comparison to the corresponding panels of FIG. 2 shows that cleaning efficacy is increased in detergent compositions of the present disclosure, based on increased removal of test soil in FIG. 2.

FIG. 8 shows photographs of stainless steel and plastic coupons that were treated with diluted detergent composition C6. Data for panels 8A and B was not obtainable because the 5% CHG that was added to detergent composition C6 was insoluble. Panel 8C shows a stainless steel coupon treated with diluted detergent composition C6 to which no CHG was added. Panel 8D shows a plastic coupon treated with diluted detergent composition C6 to which no CHG was added. For panels C and D of FIG. 8, comparison to the corresponding panels of FIG. 2 shows that cleaning efficacy is increased in detergent compositions of the present disclosure, based on increased removal of test soil in FIG. 2.

Example 5

To determine the cleaning and disinfection efficacy of detergent compositions of the present disclosure, formulation A0, according to the present disclosure and as described in Example 3, was compared to commercially available detergent composition C2 which is not according to the present disclosure. Each detergent composition (A0 and C2) was tested for the ability to remove bacterial biofilms. This was measured, first, based on the ability of treatment with the detergent composition to reduce bacterial presence and, second, based on the ability of treatment with the detergent composition to reduce protein content of the biofilm.

Biofilms comprising *Pseudomonas aeruginosa* were grown in the lumen of a test object according to the ISO/TS 15883-5 Annex F method. 8 test objects comprising *P. aeruginosa* biofilm were treated using an automated endoscope reprocessor. The treatments were performed in an automated endoscope repressor at 45° C. and at an exposure time of 8 min. In 4 of the treatments a test object was treated with diluted detergent composition AX, at a dilution factor of 1:100. In the other 4 treatments, a test object was treated with diluted detergent composition C2, at a dilution factor of 0.8:100, as recommended by the manufacturer. Subsequent to the treatment, test objects were analyzed for colony forming units (CFUs) and for total protein utilizing a BCA protein assay. These values were compared to those obtained for an untreated test object comprising the biofilm to determine fold-reduction of bacteria and percent reduction of total protein.

Results for reduction of bacteria are displayed in Table 7. In Replicate 1, treatment of a test object with diluted detergent composition A0 resulted in a $Log_{10}$-fold reduction of bacteria of 6.98 (e.g., a reduction of $10^{6.98}$-fold). In Replicate 1, treatment of a test object with diluted detergent composition C2 resulted in a $Log_{10}$-fold reduction of bacteria of 2.64 (e.g., a reduction of $10^{2.64}$-fold). In Replicate 2, treatment of a test object with diluted detergent composition A0 resulted in a $Log_{10}$-fold reduction of bacteria of 6.85 (e.g., a reduction of $10^{6.85}$-fold). In Replicate 2, treatment of a test object with diluted detergent composition C2 resulted in a $Log_{10}$-fold reduction of bacteria of 4.89 (e.g., a reduction of $10^{4.89}$-fold). In Replicate 3, treatment of a test object with diluted detergent composition A0 resulted in a $Log_{10}$-fold reduction of bacteria of 6.02 (e.g., a reduction of $10^{6.02}$-fold). In Replicate 3, treatment of a test object with diluted detergent composition C2 resulted in a $Log_{10}$-fold reduction of bacteria of 1.38 (e.g., a reduction of $10^{1.38}$-fold). In Replicate 4, treatment of a test object with diluted detergent composition A0 resulted in a $Log_{10}$-fold reduction of bacteria of 6.22 (e.g., a reduction of $10^{6.22}$-fold). In Replicate 4, treatment of a test object with diluted detergent composition C2 resulted in a $Log_{10}$-fold reduction of bacteria of 3.56 (e.g., a reduction of $10^{3.56}$-fold).

These results indicate that cleaning and disinfecting efficacy is increased in detergent compositions of the present disclosure, based on the increased removal of bacteria demonstrated by diluted detergent composition A0 in Table 7, compared to diluted detergent composition C2.

TABLE 7

$Log_{10}$-fold reduction of bacteria.

| | Diluted detergent composition A0 ($Log_{10}$-fold change) | Diluted detergent composition C2 ($Log_{10}$-fold change) |
|---|---|---|
| Replicate 1 | 6.98 | 2.64 |
| Replicate 2 | 6.85 | 4.89 |
| Replicate 3 | 6.02 | 1.38 |
| Replicate 4 | 6.22 | 3.56 |

Results for reduction of total protein are displayed in Table 8. In Replicate 1, treatment of a test object with diluted detergent composition A0 resulted in a reduction of total protein on the test object of 95.5%. In Replicate 1, treatment of a test object with diluted detergent composition C2 resulted in a reduction of total protein on the test object of 72.3%. In Replicate 2, treatment of a test object with diluted detergent composition A0 resulted in a reduction of total protein on the test object of 99.2%. In Replicate 2, treatment of a test object with diluted detergent composition C2 resulted in a reduction of total protein on the test object of 86.2%. In Replicate 3, treatment of a test object with diluted detergent composition A0 resulted in a reduction of total protein on the test object of 98.8%. In Replicate 3, treatment of a test object with diluted detergent composition C2 resulted in a reduction of total protein on the test object of 95.8%. In Replicate 4, treatment of a test object with diluted detergent composition A0 resulted in a reduction of total protein on the test object of 92.4%. In Replicate 4, treatment of a test object with diluted detergent composition C2 resulted in a reduction of total protein on the test object of 81.2%.

In each replicate shown in Table 8, cleaning and disinfecting efficacy was increased in detergent compositions of the present disclosure, based on the increased removal of total protein demonstrated by diluted detergent composition A0, compared to diluted detergent composition C2.

TABLE 8

Percent reduction of protein.

| | Diluted detergent composition A0 | Diluted detergent composition C2 |
|---|---|---|
| Replicate 1 | 95.5% | 72.3% |
| Replicate 2 | 99.2% | 86.2% |
| Replicate 3 | 98.8% | 95.8% |
| Replicate 4 | 92.4% | 81.2% |

The grammatical articles "a", "an", and "the", as used herein, are intended to include "at least one" or "one or more", unless otherwise indicated, even if "at least one" or "one or more" is expressly used in certain instances. Thus, the articles are used herein to refer to one or more than one (i.e., to "at least one") of the grammatical objects of the article. Further, the use of a singular noun includes the plural, and the use of a plural noun includes the singular, unless the context of the usage requires otherwise.

One skilled in the art will recognize that the herein described compositions, methods, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various examples have been described herein, many modifications, variations, substitutions, changes, and equivalents to those examples may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed examples. The following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the invention according to the present disclosure include, but are not limited to, the aspects listed in the following numbered clauses.

1. A detergent composition comprising:
   at least 0.001% by weight of an antimicrobial agent, based on the total weight of the composition;
   an enzyme; and
   at least 0.01% a hydrotrope, based on the total weight of the composition.
2. The composition of clause 1, wherein the hydrotrope comprises an anionic hydrotrope.
3. The composition of clause 2, wherein the anionic hydrotrope comprises at least one of an alkanoic acid, an aromatic sulfonic acid, an aromatic carboxylic acid, and a salt of any thereof.
4. The composition of clause 3, wherein the aromatic sulfonic acid is at least one of xylene sulfonic acid, cumene sulfonic acid, and a salt of any thereof.
5. The composition of any one of clauses 1-4, comprising 0.1% or less by weight of a boron-containing compound, based on the total weight of the composition.
6. The composition of any one of clauses 1-5, comprising either no boron-containing compound or only an incidental amount.
7. The composition of any one of clauses 1-6, wherein the antimicrobial agent comprises at least one of a biguanide compound and a quaternary ammonium compound.
8. The composition of clause 7, wherein the biguanide compound comprises at least one of chlorhexidine and a salt thereof.
9. The composition of any one of clauses 1-8, wherein the enzyme comprises at least one of a lipase, a protease, a peptidase, an amylase, a glycosidase, a cellulase, DNAse and a nuclease.
10. The composition of any one of clauses 1-9, wherein the composition has a pH in a range of 6 to 11.
11. The composition of any one of clauses 1-10, further comprising at least one of
    at least 0.0001% by weight of a buffer, based on the total weight of the composition, and
    at least 0.0001% by weight of a pH adjusting agent, based on the total weight of the composition.
12. The composition of any one of clauses 1-11, further comprising at least 0.01% by weight of a solvent, based on the total weight of the composition.
13. The composition of clause 12, wherein the solvent comprises at least one of a glycol ether, propylene glycol, ethylene glycol, methanol, ethanol, isopropanol, and n-propanol.
14. The composition of any one of clauses 1-13, further comprising at least one of a chelating agent and a salt.
15. The composition of any one of clauses 1-14, further comprising at least 10% by weight of water, based on the total weight of the composition.
16. The composition of any one of clauses 1-15, further comprising at least 0.005% by weight of a non-ionic surfactant, based on the total weight of the composition.
17. The composition of clause 16, wherein the non-ionic surfactant is low foam.
18. A method of making a detergent composition, the method comprising:
    combining, based on the total weight of the composition,
      at least 0.001% by weight of an antimicrobial agent,
      at least 0.01% by weight of a hydrotrope; and
      an enzyme.
19. The method of clause 18, further comprising adjusting a pH of the detergent composition prior to the adding the enzyme.
20. The method of any one of clauses 18-19, further comprising adding at least one of a buffer, a chelating agent, a solvent, water, a non-ionic surfactant, and a salt.
21. A method for cleaning an object, comprising:
    applying a detergent composition to the object, the composition comprising, based on the total weight of the composition:
      at least 0.001% by weight of an antimicrobial agent,
      at least 0.01% by weight of a hydrotrope, and
      an enzyme
    thereby cleaning the object.
22. The method of clause 21, wherein the object comprises an endoscope.
23. The method of any one of clauses 21-22, further comprising disinfecting the object.

24. The method of any one of clauses 21-23, wherein the applying the composition comprises utilizing an automated endoscope re-processor.

25. The method of any one of clauses 21-24, wherein an operating temperature is from 15° C. to 60° C.

In summary, numerous benefits have been described which result from employing the concepts described herein. The foregoing description of the one or more examples has been presented for purposes of illustration and description. It is not intended to be exhaustive or limiting to the precise form disclosed. Modifications or variations are possible in light of the above teachings. The one or more examples were chosen and described in order to illustrate principles and practical application to thereby enable one of ordinary skill in the art to utilize the various examples and with various modifications as are suited to the particular use contemplated. It is intended that the claims submitted herewith define the overall scope.

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

What is claimed is:

1. A detergent composition comprising:
   1% to 5% by weight of an antimicrobial agent, based on the total weight of the composition;
   an enzyme; and
   at least 1% by weight of a hydrotrope, based on the total weight of the composition,
   wherein the composition comprises 0.1% or less by weight of a boron-containing compound, based on the total weight of the composition
   wherein the composition comprises 10% or less by weight of a non-ionic surfactant, based on the total weight of the composition.

2. The composition of claim 1, wherein the hydrotrope comprises an anionic hydrotrope.

3. The composition of claim 2, wherein the anionic hydrotrope comprises at least one of an alkanoic acid, an aromatic sulfonic acid, an aromatic carboxylic acid, and a salt of any thereof.

4. The composition of claim 3, wherein the aromatic sulfonic acid is at least one of xylene sulfonic acid, cumene sulfonic acid, and a salt of any thereof.

5. The composition of claim 1, comprising either no boron-containing compound or only an incidental amount.

6. The composition of claim 1, wherein the antimicrobial agent comprises at least one of a biguanide compound and a quaternary ammonium compound.

7. The composition of claim 6, wherein the biguanide compound comprises at least one of chlorhexidine and a salt thereof.

8. The composition of claim 1, wherein the enzyme comprises at least one of a lipase, a protease, a peptidase, an amylase, a glycosidase, a cellulase, DNAse and a nuclease.

9. The composition of claim 1, wherein the composition has a pH in a range of 6 to 11.

10. The composition of claim 1, further comprising at least one of:
    at least 0.0001% by weight of a buffer, based on the total weight of the composition, and
    at least 0.0001% by weight of a pH adjusting agent, based on the total weight of the composition.

11. The composition of claim 1, further comprising at least 0.01% by weight of a solvent, based on the total weight of the composition.

12. The composition of claim 11, wherein the solvent comprises at least one of a glycol ether, propylene glycol, ethylene glycol, methanol, ethanol, isopropanol, and n-propanol.

13. The composition of claim 1, further comprising at least one of a chelating agent and a salt.

14. The composition of claim 1, further comprising at least 10% by weight of water, based on the total weight of the composition.

15. The composition of claim 1, further comprising at least 0.005% by weight of the non-ionic surfactant, based on the total weight of the composition.

16. The composition of claim 15, wherein the non-ionic surfactant is low foaming.

17. A method of making a detergent composition, the method comprising:
    combining, based on the total weight of the composition,
      1% to 5% by weight of an antimicrobial agent,
      at least 1% by weight of a hydrotrope; and
      an enzyme,
      wherein the composition comprises 0.1% or less by weight of a boron-containing compound, based on the total weight of the composition
      wherein the composition comprises 10% or less by weight of a non-ionic surfactant, based on the total weight of the composition.

18. The method of claim 17, further comprising adjusting a pH of the detergent composition prior to the adding the enzyme.

19. The method of claim 17, further comprising adding at least one of a buffer, a chelating agent, a solvent, water, and a salt.

20. A method for cleaning an object, comprising:
    applying a detergent composition to the object, the composition comprising, based on the total weight of the composition:
      1% to 5% by weight of an antimicrobial agent,
      at least 1% by weight of a hydrotrope, and
      an enzyme,
      wherein the composition comprises 0.1% or less by weight of a boron-containing compound, based on the total weight of the composition,
    thereby cleaning the object,
      wherein the composition comprises 10% or less by weight of a non-ionic surfactant, based on the total weight of the composition.

21. The method of claim 20, wherein the object comprises an endoscope.

22. The method of claim 20, further comprising disinfecting the object.

23. The method of claim 20, wherein the applying the composition comprises utilizing an automated endoscope re-processor.

24. The method of claim 20, wherein an operating temperature is from 15° C. to 60° C.

* * * * *